US006328746B1

(12) United States Patent
Gambale (10) Patent No.: US 6,328,746 B1
(45) Date of Patent: Dec. 11, 2001

(54) SURGICAL SCREW AND DRIVER SYSTEM

(76) Inventor: Michael A. Gambale, c/o Jordan Medical LLC, 12 Riverside Dr., Unit 1A, Pembroke, MA (US) 02359

( * ) Notice: Subject to any disclaimer, the term of this patent is extended or adjusted under 35 U.S.C. 154(b) by 0 days.

(21) Appl. No.: 09/370,637

(22) Filed: Aug. 6, 1999

Related U.S. Application Data
(60) Provisional application No. 60/095,603, filed on Aug. 6, 1998.

(51) Int. Cl.[7] .................................................. A61B 17/00
(52) U.S. Cl. ............................ 606/104; 606/73; 81/57.37; 81/434
(58) Field of Search ........................... 606/53, 61, 62, 606/63, 65, 72, 73, 104, 139, 142, 143, 144; 81/DIG. 2, 434, 57.37; 411/413, 417, 418

(56) References Cited

U.S. PATENT DOCUMENTS

| D. 385,352 | * | 10/1997 | Bales et al. . |
| 1,465,148 | * | 8/1923 | Rosenberg . |
| 3,233,500 | * | 2/1966 | De Viellier . |
| 3,703,843 | * | 11/1972 | Laverty . |
| 4,581,962 | | 4/1986 | Marbourg . |
| 5,431,660 | | 7/1995 | Burke . |
| 5,445,641 | | 8/1995 | Frigg et al. . |
| 5,683,401 | * | 11/1997 | Schmieding et al. . |
| 5,690,639 | | 11/1997 | Lederer et al. . |
| 5,735,854 | | 4/1998 | Caron et al. . |
| 5,851,219 | * | 12/1998 | Goble et al. . |
| 5,893,305 | * | 4/1999 | Liao . |
| 5,904,704 | * | 5/1999 | Goble et al. . |

OTHER PUBLICATIONS

International Search Report, PCT/US99/17790; Nov. 3, 1999.

* cited by examiner

Primary Examiner—Henry J. Recla
Assistant Examiner—William W Lewis
(74) Attorney, Agent, or Firm—Tarolli, Sundheim, Covell, Tummino & Szabo L.L.P.

(57) ABSTRACT

An improved screw and apparatus for placing screws in a wire mesh and/or bone plate during an operation. In the preferred embodiment, the screw is self-tapping and the apparatus includes color-coded screw cartridges that mount directly onto the tip of a screwdriver and are held in place until installed in the proper location as dictated by the surgeon. The cartridge fits into a magazine that can feed the screw cartridges automatically into a screw gun that drives the screw into the proper location in the bone and the wire mesh or plate, or alternatively can be used with a manual screwdriver.

15 Claims, 8 Drawing Sheets

SURGICAL SCREW AND DRIVER SYSTEM

RELATED APPLICATIONS

The present application claims all rights of priority to U.S. Provisional Application Serial No. 60/095,603 filed Aug. 6, 1998, the disclosure of which is fully incorporated herein by reference.

BACKGROUND OF THE INVENTION

Wire mesh and bone plates as methods of bone fixation have been extensively developed during the past few years. Replacement of damaged bone using metal implants is quite common and the current method of fixation has not changed for a considerable period.

Bone plates have been commonly used to replace fractured and unusable bone, particularly in neurosurgery. These preformed plates can be slightly modified by the surgeon to meet the requirements of a specific patient but, in general, are not alterable. In many instances, over a period of time, the bone grows under the plate; however, the plate remains implanted in the patient. The preformed bone plate is fixed to healthy bone by means of a number of small screws. These are small surgical screws that fit in the plate and hold it against the bone.

Wire mesh was developed to overcome some of the restrictions of bone plates. In many instances, preformed bone plates are impractical and the time necessary for the manufacture of the plate in the required form is prohibitive. Mesh was developed to allow the surgeon to form a plate that conforms to the required bone structure directly in the operating room. Mesh has undergone considerable development in design and materials. However, it is still basically an open structure with a number of fixation holes that can be cut and shaped as required. Most mesh is work-hardened, thus, once formed, it retains the required shape. Like bone plates, wire mesh is fixed to the bone by means of a number of small screws.

The current use of wire mesh for fixation of bone pieces in Reconstructive Surgery, Dentistry, Neurosurgery and Orthopedic Surgery has led to the development of multiple designs of mesh. These meshes are generally made out of a corrosion resistant material such as stainless steel or titanium, and have a multiplicity of holes for fixation to the bone by means of small surgical screws.

These surgical screws are usually small flat-head wood or sheet metal screws and are the primary means of attaching the plates or the mesh to the bone. The threads of the screws are designed for gripping the bone. The head of the screw can have any of a multiplicity of designs ranging from a straight slot, cruciate (Phillips head), hexagonal, or other such design. Due to the nature of the material used for implants, neither the screwdriver nor the screws can be of a magnetic material.

The screws are made of a material electrostatically compatible with the mesh, fit into the holes on the plate or mesh, and hold the plate or mesh against the bone. The plate or mesh is countersunk such that if the screw is attached correctly it will not protrude from the surface of the mesh. For correct contact, the screw, must, of course, be centered and perpendicular to the mesh and/or the plate. This imposes significant strain on the surgeon since he must not only keep track of these small components but must also place them absolutely straight; otherwise, the surface of the implant will not be smooth.

Current practice is to supply the mesh or bone plate in a tray with a multiplicity of screws of different sizes, to be used as required. These screws are generally not self-tapping. The surgeon selects the plate or forms the mesh according to the patient's requirements and then selects the appropriate screws for fixing the implant to the bone. He then drills the appropriate number of holes in the bone and uses a screwdriver to drive the screws into place. However, these screws used for mesh fixation are generally small, in the range of approximately one (1) to four (4) mm in length with a diameter ranging from one (1) to two (2) mm. As such, the screws are very difficult to handle even in a controlled environment. In the operating room, with its critical environment and conditions, requiring tracking of all instruments and quick efficient action, these extremely small screws create difficulties for the surgeon and staff. This creates undue stress on the surgeon who must not only place these extremely small screws into place, but must also not over-torque them during the installation, must maintain accurate alignment with the pre-drilled holes, and, above all, must not lose them in the wound. Since these screws are non-magnetic, if they "fall" into the wound they must be located and removed. If the screws are over-torqued during placement, they can shear, which adds an additional problem of removal of the sheared component from the bone and replacement.

The purpose of the present invention is to facilitate the handling, tracking and installation of these surgical screws onto the wire mesh in the operating room.

SUMMARY OF THE INVENTION

It is an object of the present invention to provide a self tapping screw that eliminates the need for pre-drilling a bone and aligning the plate in surgical procedures using wire mesh.

It is a further object of the invention to provide a means for manipulating and identifying the surgical screws, in particular, the surgical screws used for installing wire mesh and/or bone plate.

It is a further object of the invention to provide a means for tracking surgical screws, in particular, the surgical screws used in the installation of wire mesh and/or bone plate.

It is a further object of the invention to provide a means for attaching a surgical screw to a surgical screw driver such that they will remain joined until the screw is properly installed.

It is a further object of the invention to provide a means of installing surgical screws with a predefined torque.

It is a further object of the invention to provide a universal system for installation of screws that can be used on most current plates and meshes.

In accordance with the invention, a novel surgical screw, screw cartridge, surgical screw holder or magazine, and surgical screwdriver are provided herein. These components can be used independently of each other, giving the surgeon the flexibility required to deal with unique situations should they arise. However, in the preferred embodiment, they are designed to be used together as an integrated system. When used together, the components will provide an optimum method of installing a wire mesh and/or bone plate.

In accordance with one aspect of the invention, a self-tapping screw of particular design is provided herein.

In accordance with another aspect of the present invention, a surgical screw cartridge is provided herein. In the preferred embodiment, the screw cartridge is a disposable component. The cartridge facilitates manipulation of a surgical screw by a surgeon. The cartridge is preferably sized to be large enough for the surgeon to handle with gloved hands.

The cartridge provides a means for holding a surgical screw both manually and on a surgical screwdriver. This cartridge is designed to hold the screw onto the screwdriver until the screw is installed on though the wire mesh and/or bone plate into the bone, at which point the cartridge will automatically be discarded.

In a preferred embodiment, the cartridge can further be used to provide color coding of the surgical screws so that each screw size will be identified by the color of the cartridge, eliminating the possibility of mistaken screw selection. Also, the cartridge will provide a means of tracking lot numbers, and specifications of the screws.

The cartridge further provides a means for easily aligning the surgical screw with the wire mesh and/or bone plate, assuring that the screw will go in perpendicular to the surface of the mesh, providing a smooth surface, i.e., the screw flush to the wire mesh.

It is further preferred that the cartridge be constructed of a semi-rigid plastic material that will fall away of its own accord once the screw is accurately placed in the appropriate hole on the wire mesh and/or bone plate. This cartridge will be designed to work as a component of a magazine (described hereafter) or as a stand-alone item.

In accordance with a further aspect of the invention, a screw magazine is also provided herein. The screw magazine is preferably a disposable component as well. It provides a means for holding the cartridges during sterilization, transport and operation. It further can interact with the screwdriver gun (described hereafter) so that the cartridges are fed smoothly into the driver for installation. It also acts as a manual holder, should the surgeon decide to manually insert the surgical screws. The magazine can also, in the preferred embodiment, be colorcoded and lot numbered to identify the size and specification of the screws. The magazine can also be provided with whatever number of cartridges is most desirable, whether five cartridges, six cartridges, ten cartridges, some multiple of these numbers, or so forth. In a preferred embodiment, six cartridges are placed in a single magazine.

In accordance with a further aspect of the invention, a screwdriver gun is also provided herein. It is also preferred that the gun and all of its components be disposable. The screwdriver gun interacts with the magazine and cartridge to drive the screw through the appropriate hole in the wire mesh and/or bone plate into a bone, such as, for example, a cranial bone. The screwdriver further provides an easy, quick, and efficient means of installing a surgical screw. The screwdriver preferably allows the application of a finite amount of torque without causing undue shear stress on the screw. The screwdriver gun is also preferably self-loading from the screw magazine such that after every insertion of a surgical screw, the empty cartridge will be discarded into a built-in receptacle, with a new cartridge being loaded from the magazine.

In alternative embodiments, the screw gun can be configured in different shapes, i.e., with a pistol grip or with a straight handle. Ideally, the pressure exerted by the surgeon's hand will mechanically activate the gun, although a powered version of the gun may be provided as well.

DETAILED DESCRIPTION OF THE INVENTION AND THE PREFERRED EMBODIMENTS

Figure 1A:
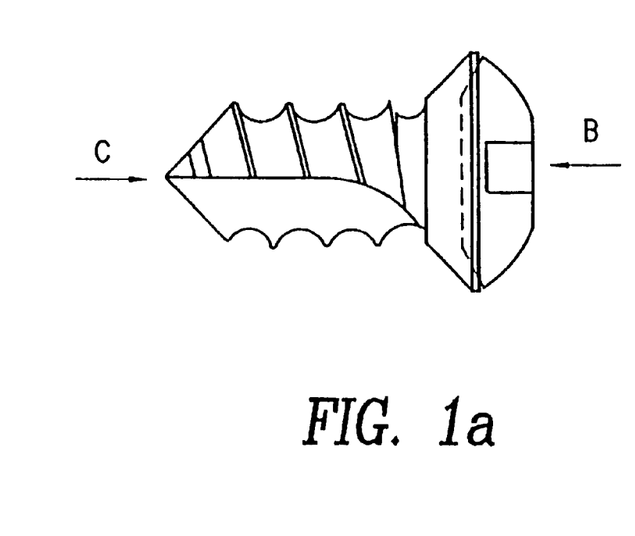
FIG. 1(a) is a side view of a self-tapping screw in accordance with the present invention.
Figure 1B:
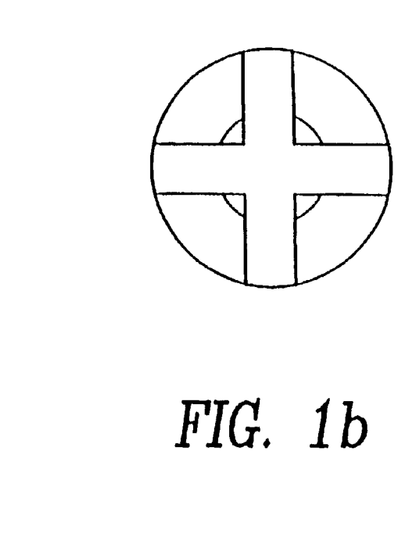
FIGS. 1(b) and 1(c) are top views and bottom views, respectively, of the screw of FIG. 1(a).
Figure 1C:
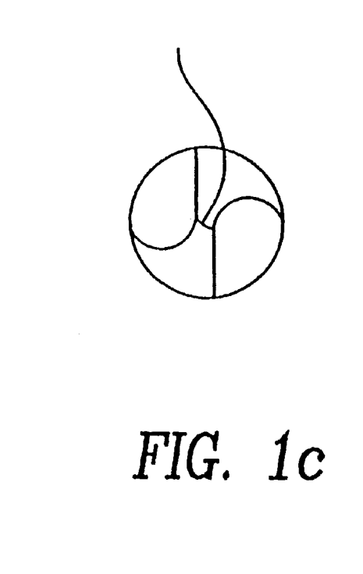

As shown in FIG. 1, a self-tapping screw is provided, particularly for use in medical procedures. The design of the screw is similar to that of a drill bit wherein the bit is further provided with screw threads.

The screw is provided with a 90° split point drill tip. This split point tip penetrates the bone quickly with minimum effort and force from the surgeon, and allows the screw to engage immediately in the bone without "walking". The split design is also self-centering, allowing the screw to penetrate vertically without angling the direction of penetration. The screw will essentially start cutting the bone wherever the tip of the screw is placed and will penetrate the bone vertical to its surface.

The screw is further provided with two cutting flutes along the entire length of the threads. These flutes facilitate chip formation and removal of the bone pieces from the cutting edge of the screw. They reducing the torque and make penetration relatively easy.

The thread design of the screw is unique. The grooves are deep and rounded to allow maximum engagement of the screw with the bone. The depth and lead of the grooves is very important in the design of the screw. The lead is in the range 40 to 50 threads per inch allowing the screw to achieve maximum penetration quickly and to maximize the contact surface with the bone while maintaining a reasonable number of threads on the screw.

In the preferred embodiment, a cruciated head is used, however, other embodiments may be provided, as well.

Other head designs may also be used to make the interface between the driver and the screw easy.

Accordingly, in the preferred embodiment, the screw is provided with a sharp 90° drill tip, including a split point head on the screw preventing it from "walking" on the bone. The screw is further provided with two flutes set at 180° along the entire length of the screw facilitating bone removal and keeping the cutting edges clean. It includes a deep groove thread design that makes it easy for the screw to hold against the bone, and a thread lead of about 40 to 50 threads per inch. The lead will be adjusted (the shorter the screw the larger the lead) based on the length of the screw.

Figure 2A:
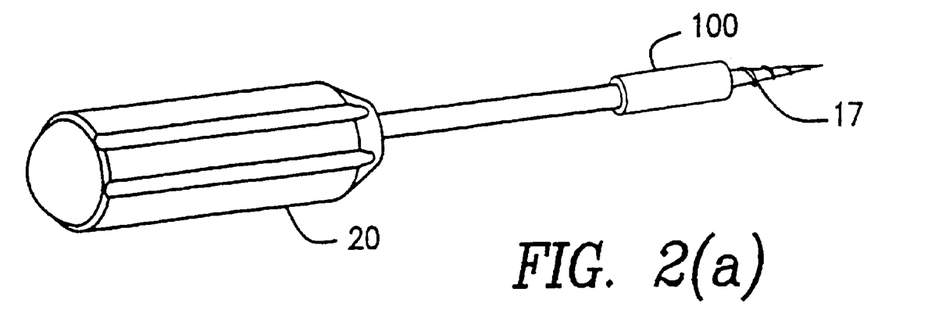
FIG. 2(a) is a perspective view of a screwdriver loaded with a cartridge thereon, in accordance with the present invention.

In accordance with a further embodiment of the present invention, as shown in FIG. 2(a), a novel surgical screwdriver is also provided herein. Surgical screwdriver 20 is provided with a cartridge 100 for holding a self-tapping screw 17. Cartridge 100 is preloaded with screw 17 prior to insertion of the screwdriver 20. In the preferred embodiment, each cartridge holds one screw.

Figure 2B:
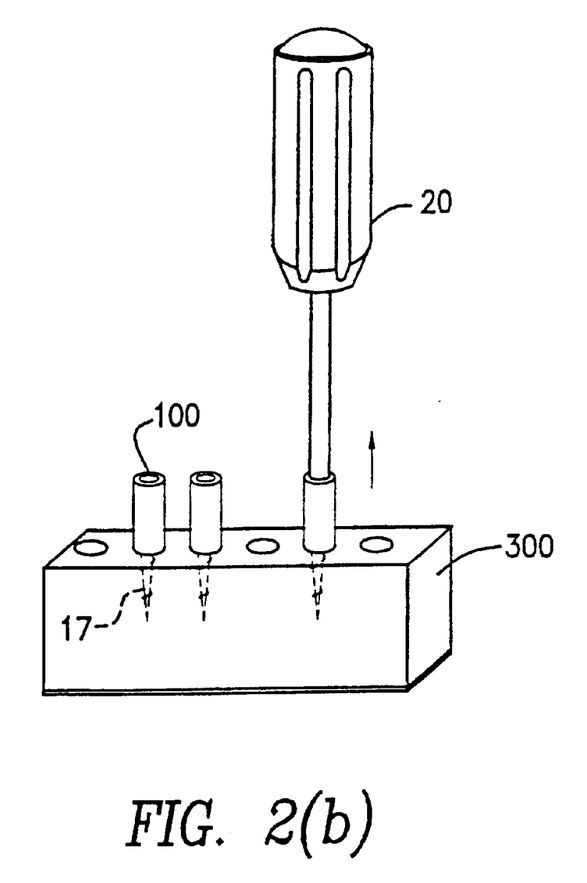
FIG. 2(b) is a perspective view of a screwdriver being removed from a magazine filled with screw cartridges, the screwdriver having a cartridge loaded thereon, in accordance with the present invention.
Figure 15:
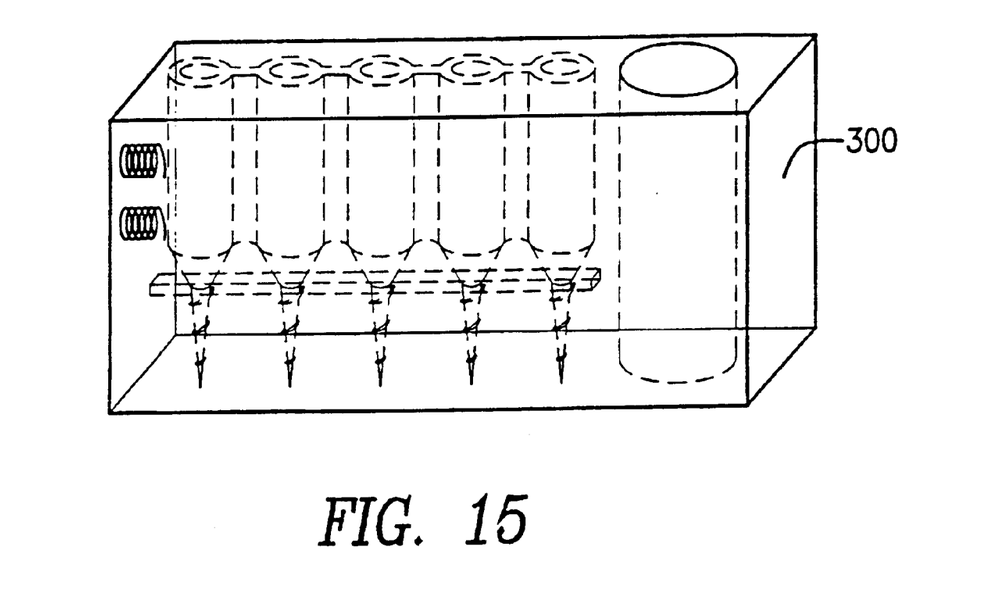
FIG. 15 is a perspective view of the cartridge magazine of FIG. 8.

As shown in FIGS. 2 and 15, a magazine 300 is preferably provided for holding a one or more cartridges 100. Each cartridge 100 is preferably preloaded with one screw 17. The magazine can be provided with any number of cartridges 100 desired.

When the surgeon is ready to use a surgical screw 17, the surgeon inserts screwdriver 20 into one of the cartridges 100 of magazine 300. Insertion of the screwdriver 20 into the cartridge 100 loads the cartridge and screw 17 onto the screwdriver. In this manner the surgeon can more easily manipulate and handle the small surgical screw 17 for insertion into a bone plate or mesh.

Figures 3, 5:
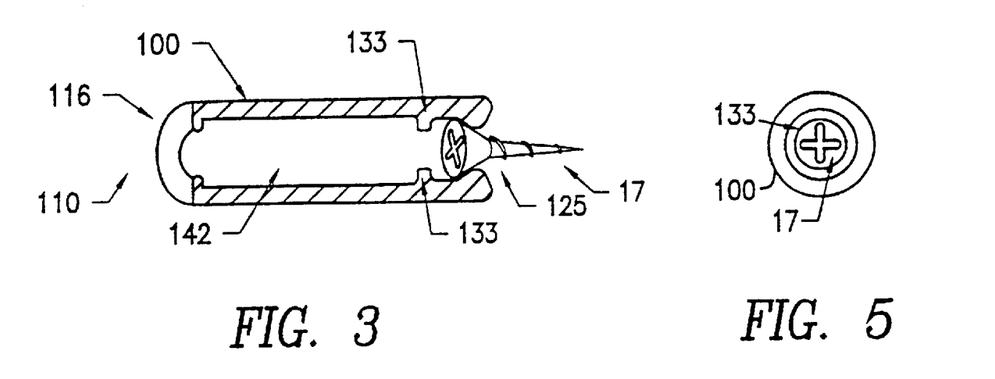
FIG. 3 is a cross-sectional view of a screw cartridge, in accordance with the present invention.
FIG. 5 is a top view of the screw cartridge of FIG. 4.

As shown in FIG. 3, cartridge 100 is preferably constructed of a material such as teflon, or nylon, although other materials may be used, as well. Cartridge 100 includes a proximal end 110 and a distal end 125. The inside of cartridge 100 is provided with an annular lip 133. Screw 17 rests up against annular lip 133 when the screw is in the preloaded position.

Figure 4:
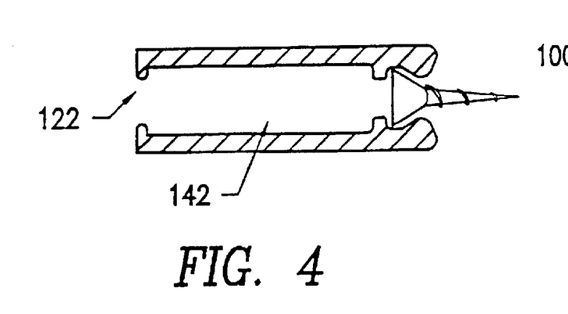
FIG. 4 is a cross-sectional view of a modified embodiment of the screw cartridge, in accordance with the present invention.
Figure 6:
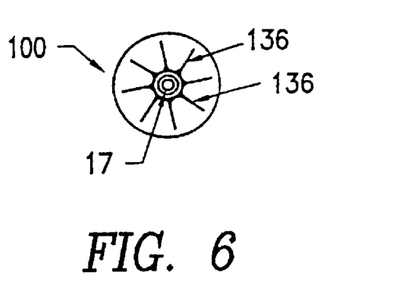
FIG. 6 is a bottom view of the screw cartridge of FIG. 4.
Figure 7:
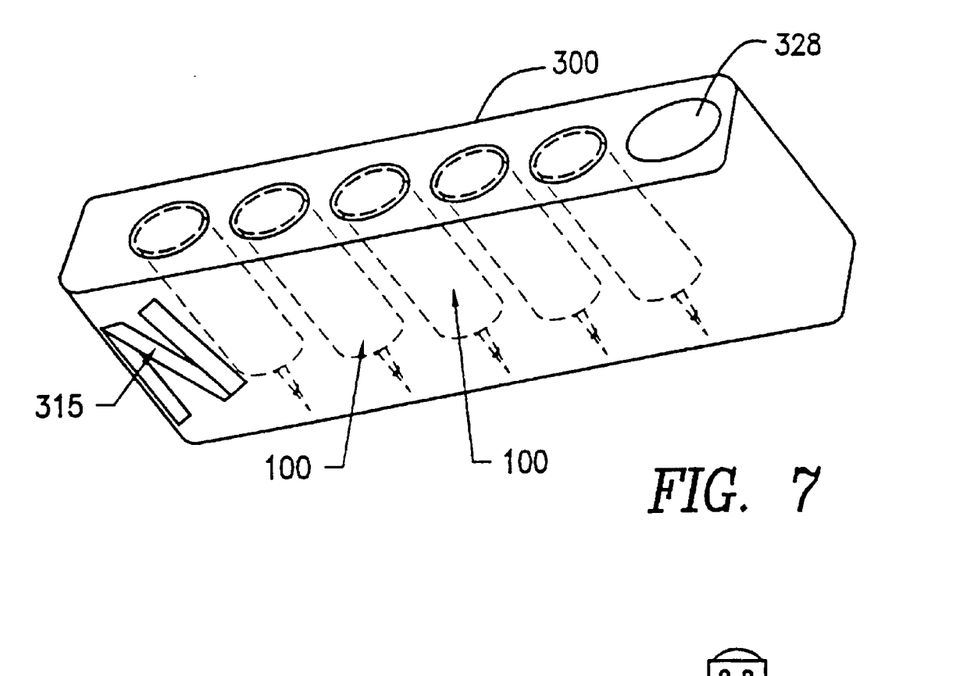
FIG. 7 is a perspective view of a cartridge magazine, in accordance with the present invention.

As shown in FIG. 4, in the preferred embodiment, cartridge 100 is preferably approximately one-quarter inch (¼") to one-half inch (½") in length from the proximal end 110 of the cartridge to distal end 125. Once preloaded, screw 17 preferably protrudes from the end of cartridge 100, as shown in FIGS. 3 and 6. Thus, with self-tapping screw 17 loaded therein, the approximate length of the combined apparatus, from the proximal end 110 of the cartridge to the tip of screw 17 is preferably approximately five-eighths (⅝") of an inch. Cartridge 100 is also preferably approximately one-eighth inch (⅛") to one-quarter inch (¼") in total diameter.

In one embodiment, cartridge 100 can be provided with a hinged or a removable endcap 116 at the proximal end 110 of the cartridge. In such an embodiment, endcap 116 is normally in place, and is be opened or removed when the surgeon is ready to insert a screwdriver into the cartridge. Alternatively, the cartridge 100 can be merely open at the proximal end, as shown in FIG. 4. In either embodiment, the cartridge is sterile and preferably within a sealed package, whether packaged seperately, or packaged preloaded into and as part of the magazine, as is preferred.

In use, a surgical screwdriver 20 is inserted into the proximal end 110 of the cartridge 100. Cartridge 100 is preferably provided with an annular lip 122 at the proximal end 110 of the cartridge. When inserting the screwdriver 20 into cartridge 100, annular lip 122 preferably presses against the screwdriver to firmly hold screwdriver 20 within the cartridge. Screwdriver 20 is inserted into the lumen 142 of cartridge 100 until the distal tip of the screwdriver engages the head of screw 17.

In one embodiment, screwdriver 20 has a narrower diameter distal portion which is easily inserted into the cartridge, with the screwdriver inserted into the lumen 142 of cartridge 100 until the annular lip 122 gently presses against a wider, proximal portion of the screwdriver. In either embodiment, pressure is provided against a portion of the screwdriver by the walls or annular lip of the cartridge (which are preferably somewhat flexible), such that the cartridge is affixed to the screwdriver. In both embodiments, the pressure exerted by the walls of the gentle or annular lip of the cartridge is gentle or moderate, such that the screwdriver shaft can easily be removed from the cartridge after insertion of the screw. The pressure exerted by the annular lip is exerted against a portion of the screwdriver proximal to the rotating screwdriver shaft such that the screwdriver shaft can, nonetheless, freely rotate while the screwdriver 20 is inserted within the cartridge.

Once the screwdriver is within the cartridge and affixed to the screw 17, the distal end 125 of cartridge 100 is preferably provided with a series of radial slots 136, as shown in FIG. 6. Radial slots 136 provide the distal end 125 of the cartridge with flexibility, allowing the distal end of the cartridge to expand or flex outward when the screwdriver shaft rotates to force the screw 17 out of the cartridge. When cartridge 100, or the distal end thereof, is constructed from nylon, at least four slots 136 should be provided to the distal end 125, to provide the suitable flexibility and elasticity necessary for expansion.

To insert a screw into a desired location, a surgeon activates or manually turns the screwdriver 20 to rotate the screw 17 as the screw is inserted through the bone plate or mesh into the bone. During rotation and exertion of pressure on the screw, the screw exits from cartridge 100, with the distal end 125 expanding in response to the applied pressure. Rotation and downward pressure is continued until the screw completely exits the cartridge and is firmly secured in the plate or mesh, and in the bone.

Figure 8:
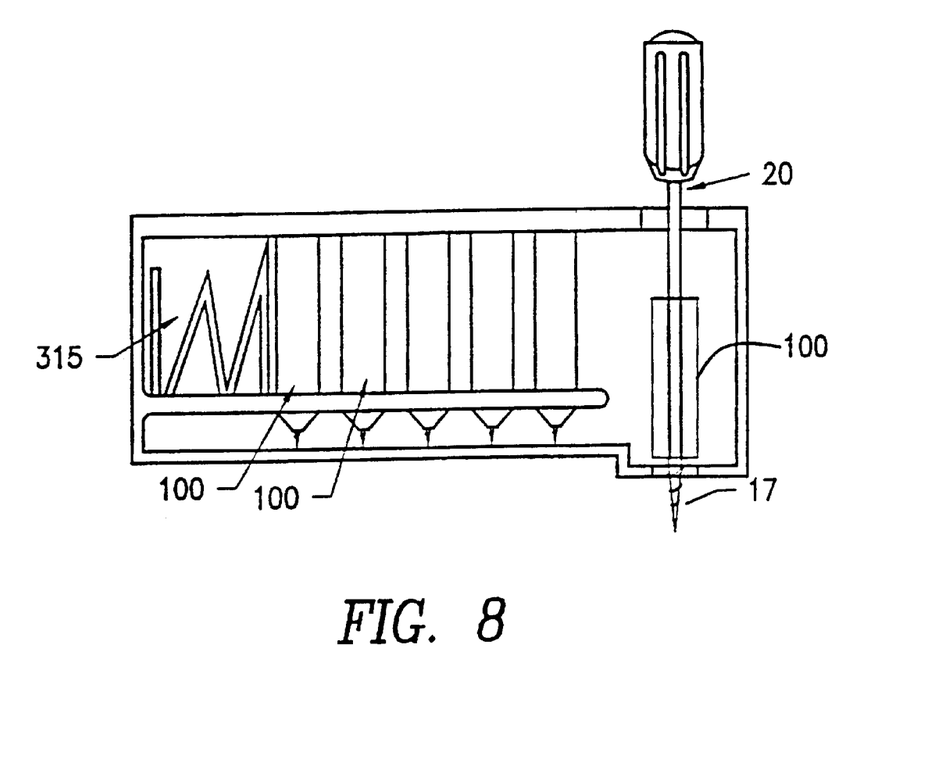
FIG. 8 is a cross sectional view of a cartridge magazine, in accordance with the present invention.
Figure 9:
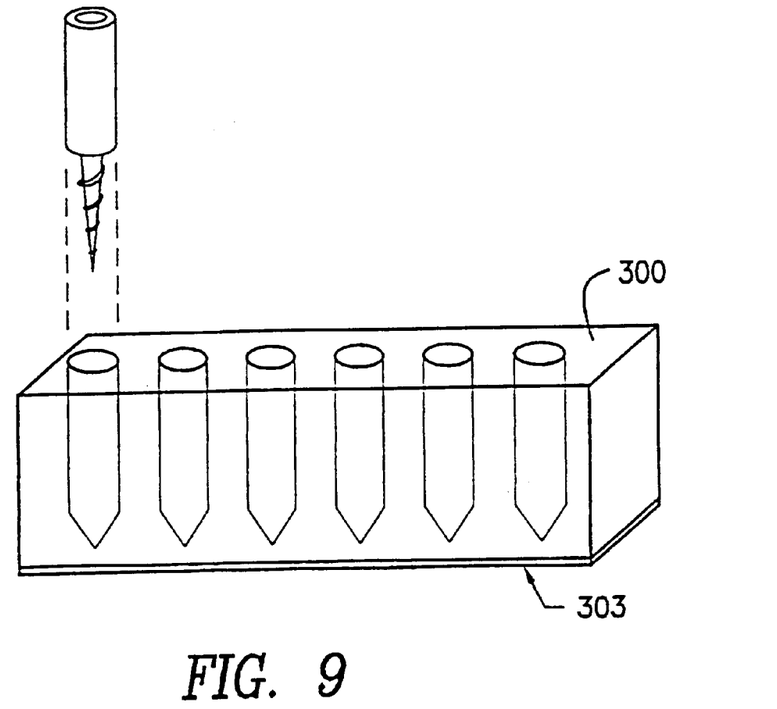
FIG. 9 is a perspective view of a cartridge magazine, with a cartridge being inserted therein, in accordance with the present invention.
Figure 10:
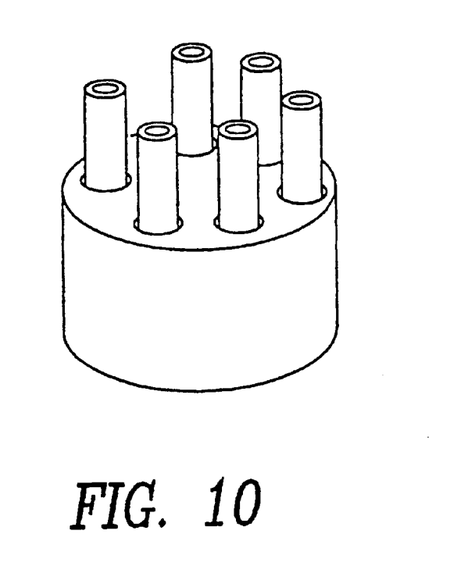
FIG. 10 is a circular cartridge magazine, in accordance with the present invention.

Cartridge magazine 300, shown for example in FIGS. 2, 7, 8, 9 and 15, is a magazine for holding a plurality of preloaded cartridges 100 therein. In one embodiment (such as in FIG. 7), the cartridge is linear or rectangular; however, other shapes, such as a circular magazine (as shown in FIG. 10) or so forth, can be provided as well. In a preferred embodiment, magazine 300 has six (6) cartridges preloaded therein. However, the cartridge can be sized to accommodate any number of cartridges desired, whether five, six, ten, some multiple thereof, or some other desired number of cartridges. In one embodiment, the magazine is approximately one to one and a half inches (1–1½") in length, one-half inch (½") in width, and three-quarters of an inch (¾") in height, as shown in FIG. 9.

In a preferred embodiment, cartridge magazine 300 consists of a clear plastic shell holding a plurality of the cartridges 100. A hole or receptacle 328 is provided at one end of the magazine 300 for insertion of a screwdriver therein. In one embodiment, the magazine merely consists of a series of receptacles for holding the cartridge 100. In a preferred embodiment, compressed leaf type or coil type spring 315 exerts a force against the plurality of cartridges 100 to press cartridges 100 toward hole 328, such that a cartridge is always loaded into the last hole or receptacle. When a cartridge 300 is located within the hole, the surgeon can insert the screwdriver 20 into hole 328 and into cartridge 100 to load the cartridge onto the screwdriver as described above, and as further shown in FIGS. 2 and 8. Once the cartridge has been loaded onto the screwdriver, the surgeon can then lift the screwdriver 20, with cartridge 100 attached thereto, out of magazine 300. The cartridge 100, with screw 17 protruding therefrom, is then fully secured to screwdriver 20 and ready for use to insert a screw into a bone plate or wire mesh.

Magazine 300 can further be provided, if desired, with an adhesive bottom 303. Adhesive bottom 303 allows the magazine to be fixedly secured to a surface, e.g. an operating table, during the course of the surgical procedure.

As an alternative to the use of a magazine such as that shown, for example, in FIGS. 2 and 15, a cartridge belt 430 can be used. In cartridge belt 430, cartridges 100 are connected together in series via a series of links 406. In this embodiment, the surgeon merely manually moves the screwdriver, preferably sequentially, from one cartridge to the next, to load each cartridge onto the screwdriver.

Figure 11:
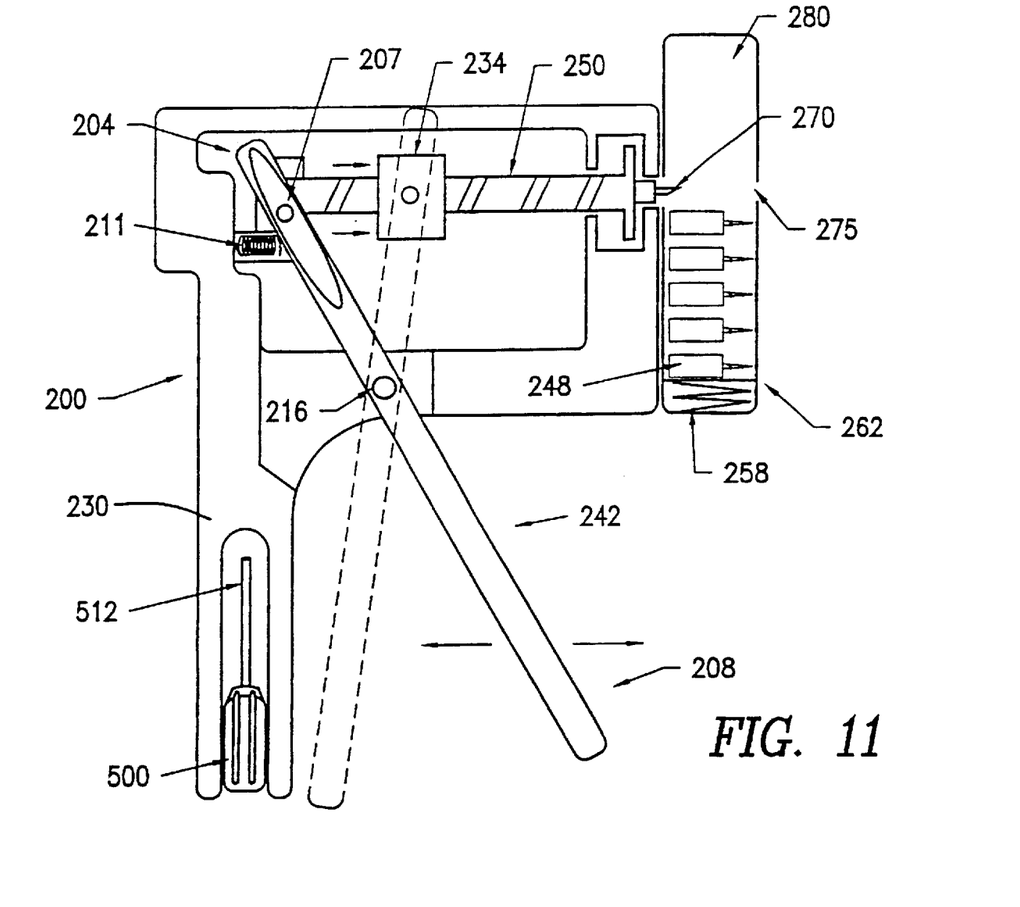
FIG. 11 is a cross-sectional view of a screw gun, in accordance with the present invention.

In an alternative embodiment to the linear screwdriver shown in FIG. 2(a), a screwdriver with a pistol-type grip, or screwdriver gun 200, can be provided, as shown in FIG. 11. Screwdriver gun 200 includes a fixed handle 230 and a movable, pivoting or trigger handle 242, trigger handle 242 having a distal end 208 where the handle 242 can be grasped by a user. Trigger handle 242 rotates about pivot 216, and is secured to drive shaft 250 at pin 207. Before use, trigger handle 242 is biased outward and away from fixed handle 230 by spring 211. Spring 211 is located below pin 207 to bias the handle 242 outward.

Figure 12:
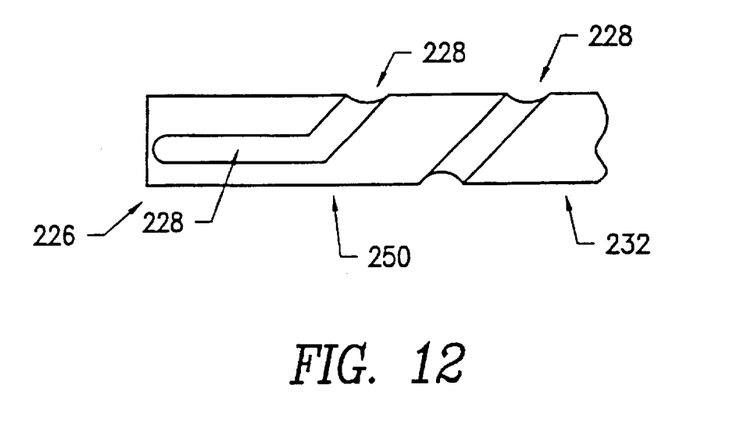
FIG. 12 is a side view of the drive shaft of the screw gun of FIG. 11.
Figure 13:
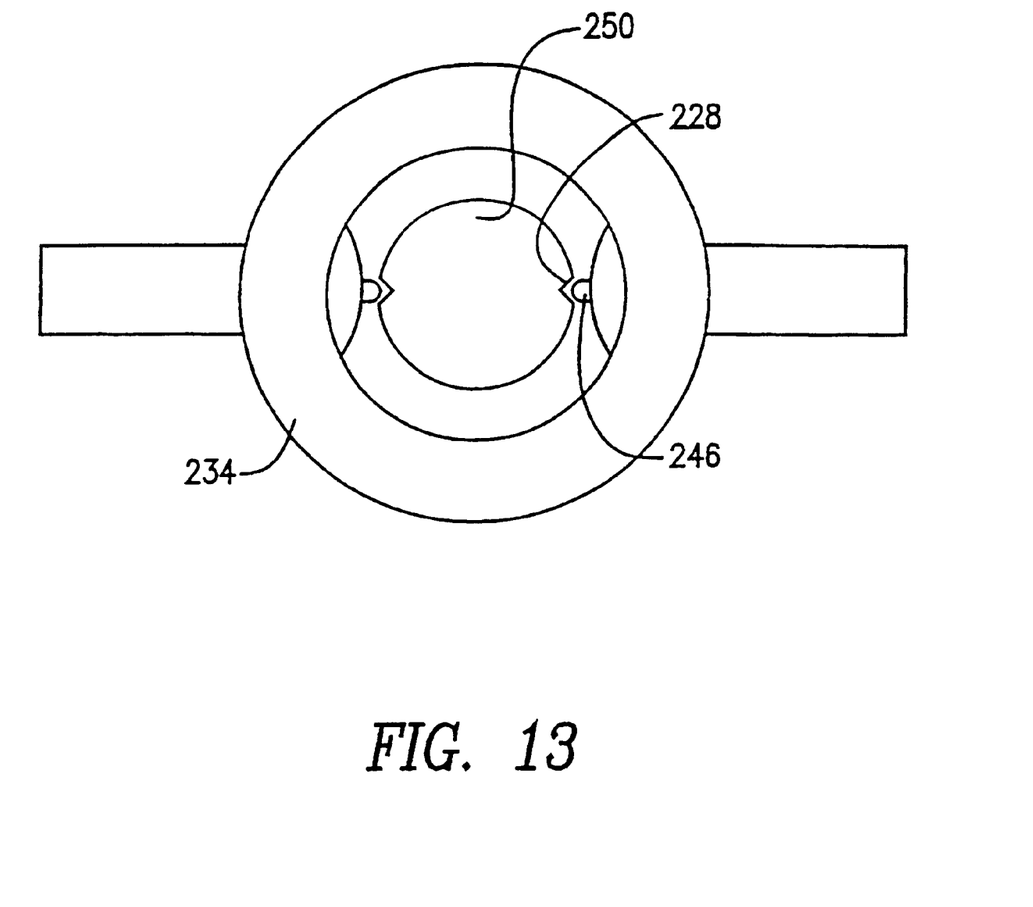
FIG. 13 is a cross-sectional view of the rider of the screw gun of FIG. 11.
Figure 14:
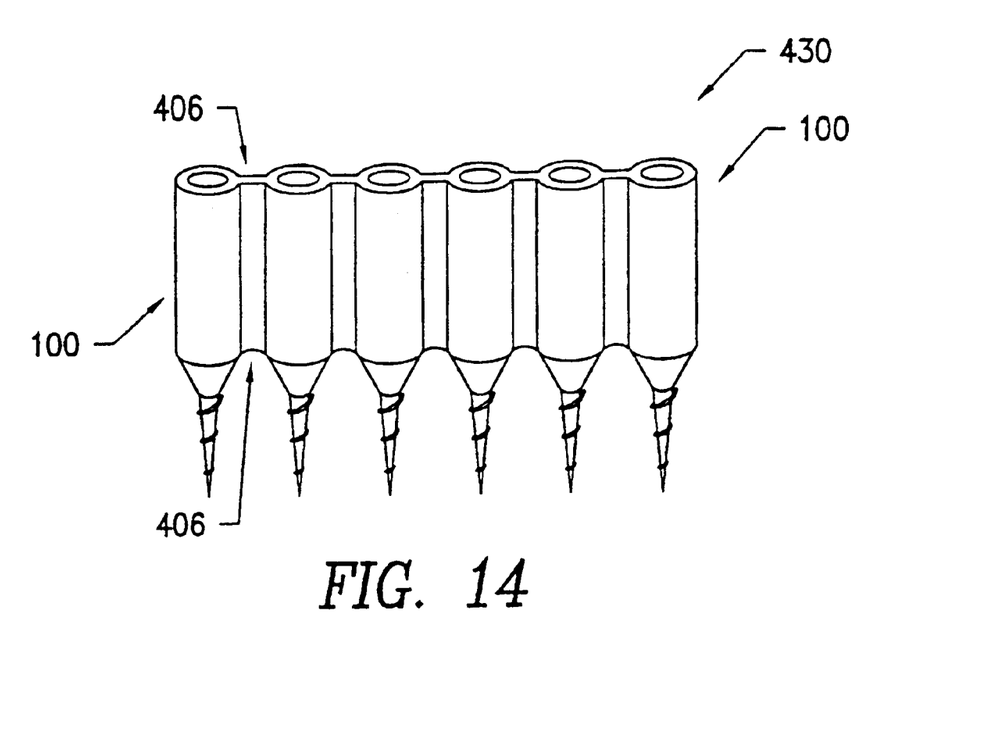
FIG. 14 is a perspective view of a linked series of cartridges, in accordance with the present invention.

Drive shaft 250 extends from the proximal end 204 of trigger handle 242 and through rider 234. As shown in FIGS. 12 and 13, drive shaft 250 is provided with a groove 228 extending along the drive shaft from the proximal end 226 of the shaft 250 to the distal end 232. Groove 228 begins as a straight slot at the proximal end 226 of the shaft, and then spirals around the drive shaft 250 toward the distal end of the shaft 232. The gun 200 is further provided with ball bearings 246 which rest between groove 228 of drive shaft 250 and the interior of rider 234, as the drive shaft sits and moves within the rider.

With the surgeon's squeezing of trigger handle 242 toward fixed handle 230, drive shaft 250 moves forward through gun 200. At the distal end of drive shaft 250 there is provided a screwdriver 270. Screwdriver gun 200 is further provided with a cartridge magazine 262, preferably at its distal end. Magazine 262 is similar in construction to magazine 300 of FIG. 2, with a spring 258 provided for exerting force on a series of cartridges 248 to bias the cartridges upward, so that the uppermost screw-loaded cartridge lines up with opening 275. When the uppermost screw-loaded cartridge has been forced upward into position, such that it is aligned with opening 275, screwdriver 270, which is attached to drive shaft 250, can move forward under the force applied to handle 208 such that the screwdriver can be inserted into a cartridge 248 to mate with a screw therein.

As force is further applied to handle 208, drive shaft 250 will continue to move forward through rider 234. As noted previously, groove 228 turns from a straight, longitudinal, slot at proximal end 226 to a slot which spirals around the drive shaft as the slot approaches distal end 232. Due to the change in the direction of the groove 228, the application of further force causes drive shaft 250 to rotate about its longitudinal axis. In this manner, the squeezing of handle 208 causes screwdriver 270 to move forward into cartridge 248 to engage a screw therein, and then causes screwdriver 270 to rotate, screwing the screw into the bone and into the bone plate or mesh. The screw is then rotated until it is secured within the mesh or plate and the bone. If desired, screwdriver 270 can further be provided with a torque-limiting clutch, to prevent overtorquing of the screw during insertion.

Once the screw has been screwed into the bone, the screwdriver gun is pulled backwards off the screw and handle 242 is released. Under the force of spring 211, the distal end 208 of handle 242 moves outward back to its resting position. This withdraws drive shaft 250, pulling screwdriver 270 backward and out of magazine 262. The just spent cartridge 248 then moves upward into storage compartment 280, which stores the spent cartridges, and a new preloaded cartridge 248 moves upward into alignment with opening 275. The screwdriver gun is then ready for another use.

In a preferred embodiment, the screwdriver gun can be provided with a small manual screwdriver 500 in a recess within handle 512. This manual screwdriver allows the surgeon to manually adjust the screw 17 once it has been inserted into the bone and the mesh or plate. Thus, the surgeon can use the screw 17 to fine tune the degree to which the screw should be further screwed in or out, once it has been initially inserted with the screwdriver gun.

In a preferred embodiment, the components of the system, i.e. the cartridge and the magazine can further be color-coded so that each screw size and/or type will be identified by the color of the cartridge and/or magazine, eliminating the possibility of mistaken screw selection. In addition, the specifications of the screw (i.e. lot number, style, type, etc.) can be imprinted or engraved on the cartridge or magazine.

Thus, in accordance with the invention, a system including a self-tapping screw is provided for screwing a surgical screw through a straight path into the bone. The system includes a cartridge that will hold the screw and release it when the screw is properly installed. Preferably, the cartridge is single use and is disposable after the screw has been affixed in the proper location. The cartridge, and the other components of the system are sterilized prior to use, whether with gamma radiation, ethylentrioxide (EtO) gas, or another means of sterilization. The cartridge will hold the screw onto the screwdriver until it is properly affixed in the appropriate location in the wire mesh or bone plate. As described above, it is preferred that the cartridge be color-coded to easily identify the size and/or type of screw. The cartridge is of a size which makes it easy for the surgeon to manipulate the cartridge using gloved hands, as opposed to directly manipulating the small surgical screws of the prior art. A series of the cartridges themselves are placed in a single magazine, to make it easy to identify, enumerate and track the numbers of screw used in a single operation.

In accordance with the invention, the system further includes a magazine for holding the screws and the cartridges. The magazine is preloaded and disposable, and provides a means for manually holding the screw cartridge while the screwdriver is being inserted. Preferably, the magazine is color-coded to identify the number and/or type of screws located therein, and has the specifications of the screws recorded on it. The magazine is also preferably marked to show the number of cartridges loaded into it. In use, the magazine can automatically eject the cartridge after it is used, or can store the spent cartridge therein. If desired, the surgeon can directly remove a single cartridge from the magazine, if necessary. A screwdriver can be inserted into the cartridge in the magazine, or alternatively, the magazine can be inserted onto a screw gun as described above. The magazine, like the other components of the system also allows easy sterilization using either gamma radiation, ethylentrioxide (EtO) gas, or another means of sterilization.

In accordance with the invention, a screw gun is also provided that can be preloaded and will install a screw using a trigger handle. The screw gun is disposable or provided for multiple use, and is used with the magazine and cartridges described above. The gun provides a finite torque for installing the screw into a bone. The screw gun is self-loading and will automatically load a new screw cartridge when the trigger is released. The screw gun will eject the spent cartridge casing, and store the spent cartridge within an appropriate compartment, e.g. in the magazine. Preferably, the screw gun is further provided with a detachable screwdriver to be used separately should the surgeon require it. As with the other components, the screwgun will allow easy sterilization either with gamma radiation, ethylentrioxide (EtO) gas, or another means of sterilization.

Having described this invention with regard to specific embodiments, it is to be understood that the description is not meant as a limitation since further embodiments, modifications and variations may be apparent or may suggest themselves to those skilled in the art. It is intended that the present application cover all such embodiments, modifications and variations.

What is claimed is:

1. Combination apparatus for improved bone fixation, comprising:
    improved bone fixation screws each having a head and thread, the improvement comprising:
        a split point tip adapted to prevent said screw from moving laterally during use; and
        two cutting flutes running substantially the entire length of said threads,
        wherein said screws are self-tapping; and
    tubular cartridges each having a hollow interior and each placeable around one of said screws, each cartridge having a proximal end and distal end, said proximal end being openable and adapted to accommodate a surgical screwdriver and said distal end being adapted to loosely retain one of said screws;
    each of said cartridges further comprising a first annular rim formed in said interior of said cartridge at said distal end of said cartridge, said annular rim adapted to receive and gently retain said head of said screw;
    each of said cartridges further comprising a second annular rim formed in said interior of said cartridge at said proximal end of said cartridge, said second annular rim adapted to rest against a screwdriver shaft inserted into said proximal end.

2. A combination apparatus for improved bone fixation according to claim 1, wherein said first and second annular rims are adapted to allow a screwdriver to be inserted into said cartridge and turn said screw while preventing said screw from falling out of contact with the screwdriver.

3. Combination apparatus for improved bone fixation according to claim 1 further comprising:
    a magazine having a magazine housing with a hollow interior and a hole disposed in said magazine housing, said magazine housing being adapted to retain a plurality of said cartridges, said hole being dimensioned to allow egress of one cartridge at a time.

4. A combination apparatus for improved bone fixation and fixing surgical screws into bone, the improvement comprising an improved screwdriver for driving surgical screws into bone, said screwdriver comprising:
    a screwdriver housing having a pistol grip;
    a trigger handle, having a proximal end and a distal end, pivotally mounted on said housing with said proximal end being spring biased away from said pistol grip;
    a drive shaft pivotally connected to said distal end of said handle at a first end of said drive shaft and having a screwdriver head at a second end of said drive shaft; and
    rotating means for rotating said drive shaft when said handle is squeezed toward said pistol grip, said rotating means comprising:
        a groove formed in said drive shaft, said groove having a straight section and a spiraled section, said straight section being straight along the longitudinal axis of said drive shaft and formed at said first end of said drive shaft, and said spiraled section spiraling around said drive shaft from said straight portion along said drive shaft towards said second end; and
        a rider, fixed to said housing, having a bore through which said drive shaft is disposed and having bearings disposed in said bore which ride in said groove.

5. A combination apparatus for improved bone fixation according to claim 4, wherein when said handle is squeezed, said drive shaft is pushed by said distal end of said handle through said rider and wherein said bearings ride along said groove, causing said drive shaft to rotate about its longitudinal axis when said spiraled section of said groove passes through said rider.

6. Combination apparatus for improved bone fixation, comprising:
    improved bone fixation screws each having a head and thread, the improvement comprising:
        a split point tip adapted to prevent said screw from moving laterally during use; and
        two cutting flutes running substantially the entire length of said threads;
        wherein said screws are self-tapping;
    tubular cartridges each having a hollow interior and each placeable around one of said screws, each cartridge having a proximal end and a distal end, said proximal end being openable and adapted to accommodate a surgical screwdriver and said distal end being adapted to loosely retain one of said screws;
    a magazine having a magazine housing with a hollow interior and a hole disposed in said magazine housing, said magazine housing being adapted to retain a plurality of said cartridges, said hole being dimensioned to allow egress of one cartridge at a time;
    a spring disposed in said interior of said magazine housing and adapted to provide a spring biasing force to said cartridges disposed in said magazine, wherein said spring biases said cartridges toward said hole in said magazine housing;
    said magazine further comprising a storage compartment for receiving and retaining said cartridges after said screw has been used from said cartridge; and
    an improved screwdriver for driving said screws into bone, said screwdriver comprising:
        a screwdriver housing having a pistol grip,
        a trigger handle, having a proximal end and a distal end, pivotally mounted on said housing with said proximal end being spring biased away from said pistol grip,
        a drive shaft pivotally connected to said distal end of said handle at a first end of said drive shaft and having a screwdriver head at a second end of said drive shaft; and rotating means for rotating said drive shaft when said handle is squeezed toward said pistol grip.

7. A combination apparatus for improved bone fixation according to claim 6 wherein said rotating means comprises:
a groove formed in said drive shaft, said groove having a straight section and a spiraled section, said straight section being straight along the longitudinal axis of said drive shaft and formed at said first end of said drive shaft, and said spiraled section spiraling around said drive shaft from said straight portion along said drive shaft towards said second end; and
a rider, fixed to said housing, having a bore through which said drive shaft is disposed and having bearings disposed in said bore which ride in said groove.

8. A combination apparatus for improved bone fixation according to claim 7, wherein when said handle is squeezed, said drive shaft is pushed by said distal end of said handle through said rider and wherein said bearings ride along said groove, causing said drive shaft to rotate about its longitudinal axis when said spiraled section of said groove passes through said rider.

9. A combination apparatus for improved bone fixation according to claim 8, wherein said hole in said magazine is a through hole passing entirely through said magazine housing, said through hole having a first end and a second end, said first end of said through hole being adapted to engage said screwdriver housing, wherein said handle is squeezed, said drive shaft enters said magazine, passes through one of said cartridges, and said screwdriver head engages said screw in said cartridge.

10. A combination apparatus for improved bone fixation according to claim 9, wherein when said screw is fixed in bone, said handle is unsqueezed, said drive shaft retracts, and said now-empty cartridge is spring biased into said storage compartment.

11. Combination apparatus for improved bone fixation, comprising:
improved bone fixation screws each having a head and thread, the improvement comprising:
a split point tip adapted to prevent said screw from moving laterally during use; and
two cutting flutes running substantially the entire length of said threads;
wherein said screws are self-tapping; and
an improved screwdriver for driving said screws into bone, said screwdriver comprising:
a housing having a pistol grip;
a trigger handle, having a proximal end and a distal end, pivotally mounted on said housing with said proximal end being spring biased away from said pistol grip;
a drive shaft pivotally connected to said distal end of said handle at a first end of said drive shaft and having a screwdriver head at a second end of said drive shaft; and
rotating means for rotating said drive shaft when said handle is squeezed toward said pistol grip, said rotating means comprising:
a groove formed in said drive shaft, said groove having a straight section and a spiraled section, said straight section being straight along the longitudinal axis of said drive shaft and formed at said first end of said drive shaft, and said spiraled section spiraling around said drive shaft from said straight portion along said drive shaft towards said second end; and
a rider, fixed to said housing, having a bore through which said drive shaft is disposed and having bearings disposed in said bore which ride in said groove.

12. A combination apparatus for improved bone fixation according to claim 11, wherein when said handle is squeezed, said drive shaft is pushed by said distal end of said handle through said rider and wherein said bearings ride along said groove, causing said drive shaft to rotate about its longitudinal axis when said spiraled section of said groove passes through said rider.

13. Combination apparatus for improved bone fixation, comprising:
improved bone fixation screws each having a head and thread, the improvement comprising:
a split point tip adapted to prevent said screw from moving laterally during use; and
two cutting flutes running substantially the entire length of said threads;
wherein said screws are self-tapping;
tubular cartridges each having a hollow interior and each placeable around one of said screws, each cartridge having a proximal end and a distal end, said proximal end being openable and adapted to accommodate a surgical screwdriver and said distal end being adapted to loosely retain one of said screws; and
an improved screwdriver for driving said screws into bone, said screwdriver comprising:
a housing having a pistol grip;
a trigger handle, having a proximal end and a distal end, pivotally mounted on said housing with said proximal end being spring biased away from said pistol grip;
a drive shaft pivotally connected to said distal end of said handle at a first end of said drive shaft and having a screwdriver head at a second end of said drive shaft; and
rotating means for rotating said drive shaft when said handle is squeezed toward said pistol grip, said rotating means comprising:
a groove formed in said drive shaft, said groove having a straight section and a spiraled section, said straight section being straight along the longitudinal axis of said drive shaft and formed at said first end of said drive shaft, and said spiraled section spiraling around said drive shaft from said straight portion along said drive shaft toward said second end; and
a rider, fixed to said housing, having a bore through which said drive shaft is disposed and having bearings disposed in said bore which ride in said groove.

14. A combination apparatus for improved bone fixation according to claim 13, wherein when said handle is squeezed, said drive shaft is pushed by said distal end of said handle through said rider and wherein said bearings ride along said groove, causing said drive shaft to rotate about its longitudinal axis when said spiraled section of said groove passes through said rider.

15. A combination apparatus for improved bone fixation according to claim 14, wherein when said handle is squeezed, said screwdriver head is adapted to pass through one of said cartridges and engage said screw in said cartridge.

* * * * *